United States Patent
Chihani

(10) Patent No.: US 6,521,813 B1
(45) Date of Patent: Feb. 18, 2003

(54) LIQUID ACQUISITION LAYER FOR ABSORBENT ARTICLES

(75) Inventor: Thami Chihani, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/308,812

(22) PCT Filed: Nov. 26, 1997

(86) PCT No.: PCT/SE97/01983

§ 371 (c)(1),
(2), (4) Date: May 26, 1999

(87) PCT Pub. No.: WO98/25560

PCT Pub. Date: Jun. 18, 1998

(30) Foreign Application Priority Data

Dec. 11, 1997 (SE) ............................................. 9604553

(51) Int. Cl.⁷ ................................................ A61F 13/20
(52) U.S. Cl. ...................................................... 604/384
(58) Field of Search .............................. 604/378, 379, 604/383, 380, 368, 384, 385.01, 367

(56) References Cited

U.S. PATENT DOCUMENTS

| | | | | |
|---|---|---|---|---|
| 3,604,422 A | * | 9/1971 | Sabes | 604/365 |
| 3,967,623 A | * | 7/1976 | Butterworth et al. | 602/45 |
| 4,016,319 A | * | 4/1977 | Marshall | 428/113 |
| 4,519,799 A | * | 5/1985 | Sakurai et al. | 604/366 |
| 4,676,784 A | * | 6/1987 | Erdman et al. | 604/368 |
| 4,842,595 A | * | 6/1989 | Nakanishi et al. | 604/372 |
| 5,431,643 A | * | 7/1995 | Ouellette et al. | 604/358 |
| 5,722,966 A | * | 3/1998 | Christon et al. | 604/364 |
| 5,763,044 A | * | 6/1998 | Ahr et al. | 428/119 |
| 5,919,177 A | * | 7/1999 | Georger et al. | 156/163 |
| 6,087,551 A | * | 7/2000 | Pereira | 604/358 |
| 6,258,997 B1 | * | 7/2001 | Johansson et al. | 604/378 |

FOREIGN PATENT DOCUMENTS

| | | |
|---|---|---|
| BE | 1 007 041 | 2/1995 |
| EP | 0 737 462 | 10/1996 |
| GB | 2 171 016 | 8/1986 |

* cited by examiner

Primary Examiner—Dennis Ruhl
Assistant Examiner—Linh Truong
(74) Attorney, Agent, or Firm—Young & Thompson

(57) ABSTRACT

An absorbent article, such as a sanitary napkin, a panty-liner, or a diaper includes a carrier layer against which individual fibers, detached from each other and each exhibiting two fiber ends, are attached with one fiber end against the carrier layer. There is an attachment angle α between the carrier layer and each individual fiber. The individual fibers have at least a first fiber type and a second fiber type. The absorbent article further includes a liquid-pervious cover layer and a liquid acquisition layer.

19 Claims, 5 Drawing Sheets

LIQUID ACQUISITION LAYER FOR ABSORBENT ARTICLES

TECHNICAL FIELD

The invention pertains to a liquid acquisition layer for an absorbent article such as a sanitary napkin, an incontinence protector, a diaper, a panty-liner, a bed protector or the like, which exhibits a carrier layer against which individual fibres, detached from each other and each exhibiting two fibre ends, are attached with one fibre end against the carrier layer with an attachment angle α between the carrier layer and each individual fibre. The invention also relates to an absorbent article provided with the liquid acquisition layer.

BACKGROUND OF THE INVENTION

Great demands are made on both softness and dryness of liquid acquisition layers for absorbent articles of the herein intended type, which are intended to be in contact with the body of the user during use.

However, it has proved to be difficult to achieve a liquid acquisition layer having a soft and textile-like surface which at the same time remains dry during use.

One problem, when using nonwoven materials or other similar textile materials as liquid acquisition layers for absorbent articles, is that the fibre structure of the material absorbs liquid when the cover layer is wetted. A certain quantity of the liquid is not conducted downwards to the underlying absorbent structure, but remains instead in the liquid receiving cover layer. Since the liquid receiving cover layer is in contact directly against the body, such articles are perceived as being wet and uncomfortable to wear already after an initial wetting. Furthermore, the wet surface which is in direct contact with the skin results in an increased risk of skin irritation and infections.

The main reason for part of the liquid remaining in textile cover layers is that such textile materials usually consist of an irregularly shaped fibre structure with fibres or fibre filaments directed along the plane of the material. This implies that excreted body fluid, by means of the capillary action of the fibres, is distributed along the fibre structure in the direction of the plane of the material. Also liquid which is not absorbed by the fibre capillaries is conducted along the fibre structure in the plane of the material and is collected in voids between the fibres, where the liquid remains without being able to be further distributed to materials on the inside. These factors result in a certain amount of the liquid remaining in the cover layer and create a wet surface closest to the user.

Another problem with the present nonwoven materials, having fibres primarily directed along the material plane, is that the possibility to control the wetting course, by utilizing different types of fibres exhibiting differences in properties such as for example wettability, is limited. Furthermore, the possibility to control the wetting course is limited where the location of the fibres and their design are concerned.

Particularly with regard to the sanitary napkins and panty-liners of today, which should be discreet to wear during use, another problem is that such articles, in order to obtain a liquid absorbent structure and at the same time maintain a dry surface closest to the user, are built up from a number of layers exhibiting essentially different properties. This implies that such articles are rather voluminous and therefore often are perceived as being uncomfortable and indiscreet. A further disadvantage with having a number of layers is that the material consumption for these disposable articles is high, which results in a high manufacturing cost and a high usage of raw material.

From U.S. Pat. No. 3,967,623 it is known to use a liquid-pervious cover layer consisting of a perforated plastic layer as a carrier material, on which fibres treated with wetting agent are applied in order to create a soft and fluffy surface. The individual fibres are oriented so that they are directed upwards towards the user during use and are approximately 5 mm long. Since the fibres are directed upwards towards the user, a soft and fluffy surface is created. However, the problem that the liquid transfer from the fibres to the absorbent body on the inside is poor remains to be solved, which results in the surface closest to the user remaining wet after the initial wetting.

BE 09300552 relates to a cover layer for an absorbent article, which cover layer consists of a plastic film, which at least on one side is covered with fibres which are not fused together and which are attached at an angle towards the plastic film. In order to obtain such a structure the fibres may, for example by means of flocking, be attached with one of their fibre ends against a melted fibre fixation layer on the plastic film. The plastic film can be perforated so that the material becomes liquid-pervious. The fibres are between 0.3 and 2.5 mm long and the thickness may vary depending on how soft the layer should be. Different fibres may be used, such as for example viscose, cotton, polyethylene, polypropylene, polyester, and polyamide. The risk of the liquid spreading in the material plane, and consequently along the surface of the cover layer, is minimal with this previously known cover layer. Furthermore, the cover layer exhibits a soft surface closest to the user. However, the problem of achieving a dry surface remains with this previously known cover material, when the layer is used as a liquid-pervious surface material on an absorbent article.

SUMMARY OF THE INVENTION

The problems with achieving a liquid acquisition surface, for, for example, liquid-pervious cover layers intended for absorbent articles or for liquid acquisition articles, such as for example a panty-liner, which liquid acquisition surface is soft and exhibits a dry surface also after wetting, have been substantially eliminated by the present invention.

Accordingly, a soft, skin-friendly and textile-like liquid acquisition layer for an absorbent article has been achieved by means of the invention, which layer has an ability to conduct the liquid downwards in the structure and, by means of this, to maintain a dry surface closest to the user.

A liquid acquisition layer according to the invention exhibits a carrier layer against which separate fibres, detached from each other and each exhibiting two fibre ends, are attached with one fibre end against the carrier layer with an attachment angle α between the carrier layer and each individual fibre. The liquid acquisition layer is primarily characterized in that the individual fibres comprise at least a first fibre type and a second fibre type. Since the fibres are not bonded together into a nonwoven fabric but instead are oriented so that an angle arises between the fibre and an underlying carrier material, accordingly, increased possibilities are obtained to design a cover layer which utilizes the properties of different fibres, for example the liquid-conducting ability of different fibres.

According to a preferred embodiment, the fibres of the first fibre type are longer than the fibres of the second fibre type. Thereby, the fibres of the first fibre type are suitably 0.3–1.5 mm long, while the fibres of the second fibre type are 1.5–5 mm long. The fibre length is dependent on the other properties of the fibres, such as for example their liquid absorption ability. Furthermore, the fibre length is dependent on which type of absorbent article the liquid acquisition layer is intended for, since urine and menstrual fluid are different from each other, among other things with regard to viscosity and surface energy. This implies that the length of the fibres must be adapted to these conditions in order to achieve an optimum liquid acquisition layer with regard to dryness and softness.

According to one embodiment, the longer fibres are more hydrophobic than the shorter fibres. Since the longer fibres which are located closer to the skin of the user during use are more hydrophobic than the shorter fibres, a distance is created between the skin and the shorter liquid-absorbing fibres. Accordingly, the more hydrophillic fibres are constituted by fibres which exhibit a lower contact angle in contact with body fluid than the more hydrophobic fibres. The hydrophillic fibres may, for example, be constituted by cellulose, viscose, polyester or hydrophobic fibres treated with wetting agent, such as for example polyolefin fibres treated with wetting agent. The longer and more hydrophobic fibres are for example constituted by untreated polyolefin fibres. The advantage with this embodiment is that the surface closest to the body is kept dry also when repeated wettings occur, and the risk of the liquid spreading along the plane of the liquid acquisition layer is nearly eliminated.

According to another embodiment, a difference is obtained in the liquid absorption ability of the fibre types by means of the shorter fibres exhibiting finer capillaries, i.e. a smaller pore radius than the longer fibres. Accordingly, a liquid gradient from regions with longer fibres having larger capillaries to the shorter fibres having finer capillaries is created. Thereby, the liquid is mainly absorbed in regions with shorter fibres, which implies that the surface closest to the user remains dry. An advantage with this embodiment is that both fibre types can be constituted by the same material, whereby the difference in liquid absorption ability is obtained by means of the fibre types exhibiting differences in pore radius. Still another possibility to control the liquid absorption/liquid conducting ability of the fibre regions is achieved by means of the regions with the shorter fibres exhibiting a higher fibre density than the regions with the longer fibres. As a result of this, fine external cavities, i.e. external capillaries, are created in the regions with the shorter fibres, something which results in a higher liquid absorption/liquid conducting ability between the fibres in these regions.

According to another embodiment, the two fibre types exhibit different geometry. For instance, the second fibre type is constituted by fibres having a branched cross-section, such as the fibres described in WO 93/01779. Since the fibres exhibit a branched cross-section, cavities are created, i.e. external capillaries between the fibres, resulting in an increased liquid absorption ability.

The second fibre type may further be constituted by fibres which collapse, i.e. shrink, when they are wetted. When wetting of such a liquid acquisition surface occurs, the distance between the user and the liquid-absorbing fibres is improved. The geometrical construction of the fibres may of course adopt other shapes, resulting in an increased distance between the user and the liquid-absorbing fibres and/or improving the liquid absorption/liquid conducting ability of the second fibre type. The first fibre type is preferably constituted by fibres which are hydrophobic, such as for example polyolefin fibres, or other fibres suitable for the purpose.

According to still another embodiment, the fibre types exhibit a difference in stiffness. Since the first fibre type having longer fibres exhibits a lower stiffness than the second fibre type, a soft surface is created against the user at the same time as the stiffer and shorter fibre provides the liquid acquisition layer with stability. Accordingly, the risk of the article being creased during use is minimized. This implies that the article is more comfortable to wear, and the risk of the body fluid leaking out to the panties of the user because of creasing of the article is nearly eliminated.

According to one embodiment, the angle $\alpha$ between the carrier layer and each individual fibre is between 30–90°.

According to one embodiment, the angle $\alpha$ between the carrier layer and each individual fibre is approximately 90°, but may of course vary slightly between the different fibres. The advantage with such an embodiment is that the body fluid rapidly is conducted in a direction straight downwards into the absorbent structure and, accordingly, the risk of the article being perceived as wet is minimized.

According to another embodiment, the angle $\alpha$ between the carrier layer and each individual fibre is between 30–70°.

By means of this embodiment, the surface maintains a clean and dry visual appearance also after use, since the shorter wet fibres are not visible when the user observes the sanitary napkin from above.

According to one embodiment, the cover layer exhibits a regularly alternating pattern comprising portions of fibres of the first fibre type and portions of fibres of the second fibre type. Since the cover layer thus comprises regions with fibres of different length, where the longer fibres create raised barriers, a distance is created between the skin and the liquid-absorbing fibres. Furthermore, liquid is prevented from spreading across the surface of the cover layer which is in direct contact against the user during use. The alternating pattern may be arranged in rows, checks, or in another pattern advantageous for the manufacture and use. Furthermore, the proportion of long fibres in relation to the proportion of short fibres may vary across the surface of the cover layer, as may the fibre density and the dimension of the alternating pattern. Factors which affect the selection of the above-mentioned pattern structure are the properties of the fibre types, such as for example their liquid absorption ability. The properties of the carrier material are also of importance. Furthermore, it is of essential significance which type of liquid the article is intended to absorb. As earlier mentioned, urine and menstrual fluid exhibit differences, for example with regard to viscosity and surface energy. A liquid-pervious cover layer for different types of articles exhibiting a reduced surface wetness and an increased softness may accordingly be obtained by means of the possibility to vary the pattern structure.

Since the article rapidly is saturated with liquid within the region around the wetting site, i.e. within the region of the crotch portion of the article which the body fluid reaches first, the carrier layer of the cover layer, according to a preferred embodiment, exhibits a regularly alternating pattern exhibiting separated regions of fibres of the first fibre type and a substantially continuous region of fibres of the second fibre type. The continuous region with liquid-absorbing fibres facilitates the transport of the liquid from the wetting zone to the remaining parts of the liquid acquisition layer of the article. Accordingly, the risk that the liquid acquisition layer is saturated with liquid within the wetting zone, with accompanying risk of leakage, is eliminated.

According to another embodiment, the cover layer exhibits continuous regions of the different fibre types, for example in a row pattern along the longitudinal direction of the article. Also in this embodiment, the advantage is that the liquid can be distributed out towards the end portions of the article and the risk of the area around the wetting site being saturated with liquid, with leakage as a consequence, is thus eliminated.

According to another embodiment, the entire carrier layer of the cover layer comprises both fibres of the first fibre type and fibres of the second fibre type, which are uniformly distributed across the entire surface of the carrier layer. In this way a material is achieved which across the entire surface has short and long fibres, respectively. An advantage with such an embodiment is that the cover layer is easy to manufacture, since no synchronization problems will arise. A further advantage with such an embodiment is that the cover layer looks dry even during use, since the short and liquid-absorbing fibres are hidden by the longer and more hydrophobic fibres.

A further embodiment comprises a cover layer exhibiting separated regions of the first fibre type and separated regions of the second fibre type. This embodiment may be advantageous when the risk of the liquid remaining in the cover layer already is eliminated, for example when an underlying absorbent structure effectively drains the cover layer of liquid. Another advantage with such an embodiment is that the liquid distribution in the cover layer is reduced.

Furthermore, the invention includes an absorbent article such as a sanitary napkin, a panty-liner, a diaper, or the like comprising an absorbent body enclosed in a cover wherein at least a portion of the cover consists of a liquid-pervious cover layer. The liquid-pervious cover layer comprises a carrier layer against which individual fibres, detached from each other and each exhibiting two fibre ends, are attached with one fibre end against the carrier layer. Between the cover layer and each individual fibre an attachment angle arises. The individual fibres comprise at least a first fibre type and a second fibre type, where the fibres of the first fibre type are longer than the fibres of the second fibre type. Furthermore, the fibres of the first fibre type are more hydrophobic that the fibres of the second fibre type.

According to still another embodiment, the liquid-pervious cover layer of the article is designed so that the cover layer within the crotch region primarily exhibits fibres of the first fibre type. Accordingly, the liquid-pervious cover layer primarily exhibits short, hydrophillic fibres within the crotch region, while the cover layer in the two end portions primarily exhibits long, hydrophobic fibres. By means of this, a cover layer is obtained which only exhibits a wet region within the crotch region of the article during use.

According to a similar embodiment of the article, the liquid-pervious cover layer is designed so that the central portion of the crotch region at least substantially comprises fibres of the second fibre type and that the two edge portions of the crotch region at least substantially comprise fibres of the first fibre type. Furthermore, the cover layer within the two end portions primarily comprises fibres of the first fibre type. The embodiment is similar to the preceding one, but since the liquid-pervious cover layer along the entire edge portion of the article comprises fibres which are longer and more hydrophobic than the fibres in the central portion of the crotch region, this implies that the risk of the liquid spreading out on the side edges of the article and leaking further to the pants of the user is nearly eliminated.

Still another embodiment is constituted by a panty-liner or a similar absorbent article, where only a minor absorption capacity is necessary. According to this embodiment, the carrier layer in the liquid acquisition layer is liquid-impervious and, accordingly, constitutes the backing material of the article. According to the invention, individual fibres detached from each other are attached in one of the two ends of the fibre, with an attachment angle between the carrier layer and each individual fibre, against the side of the liquid-impervious carrier layer which is intended to be in contact with the user during use. The individual fibres at least comprise a first fibre type and a second fibre type, where the fibres of the first fibre type are longer than the fibres of the second fibre type. Furthermore, the shorter fibres are liquid-absorbing while the longer fibres not are liquid-absorbing. Regions with the longer fibres serve as raised barriers between the user and the shorter liquid-absorbing fibres during use. An advantage with this embodiment is that the shorter fibres in the cover layer have an ability to absorb liquid, which implies that no further absorbent structure is necessary. Accordingly, the material consumption for these articles is reduced, which results in a lower manufacturing cost and a lower raw material use. Still another advantage with such articles is that they are thinner and thus more comfortable and more discreet to wear.

BRIEF DESCRIPTION OF THE DRAWINGS

In the following, the invention will be described in greater detail with reference to the figures shown in the attached drawings, wherein.

DETAILED DESCRIPTION OF PREFERRED EMBODIMENTS

Figure 1:
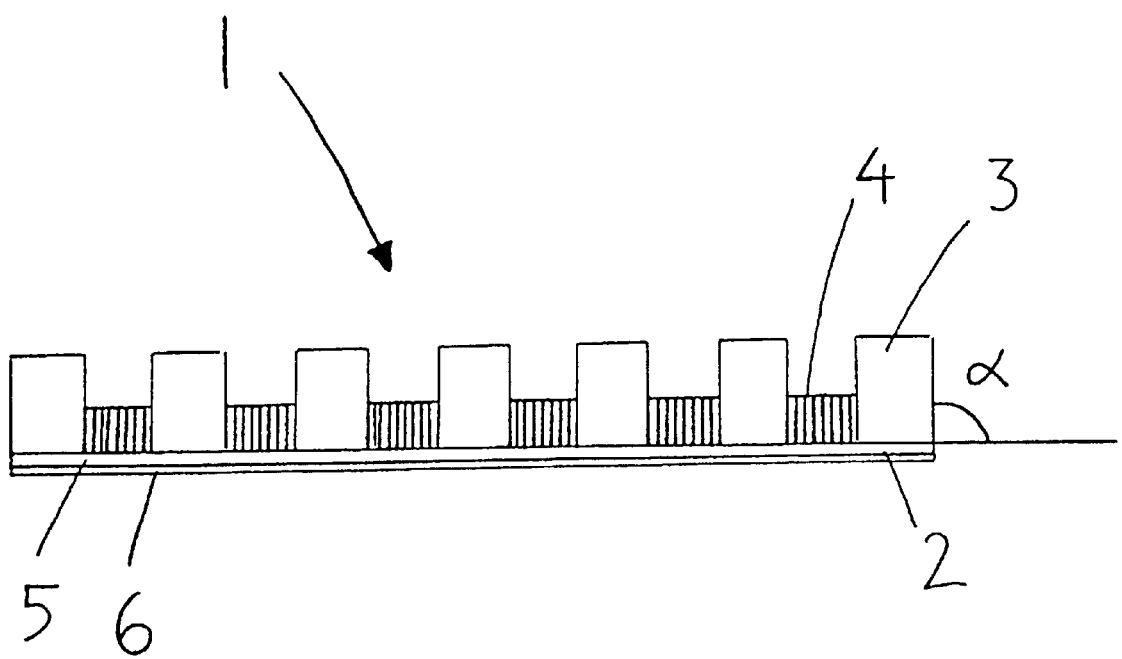
FIG. 1 shows a cross-section through a liquid acquisition layer according to the invention.

The liquid acquisition layer 1 shown in FIG. 1 consists of a carrier layer 2 on which fibres 3, 4 are attached. The fibres 3, 4 are attached on the carrier layer 2 with one of their ends, while the other, free end is directed away from the carrier layer, wherein the individual fibres are arranged with an angle $\alpha$ to the carrier layer. The attachment angle $\alpha$ is approximately 90° in the shown example, but may of course vary somewhat between the different fibres.

The fibres are attached to the carrier material for example by means of flocking, whereby one fibre end is attached against a melted fibre fixation layer. The fibres 3, 4 consist of a first fibre type 3 and a second fibre type 4. The fibres of the first fibre type 3 are longer than the fibres of the second fibre type 4. The fibre length of the two fibre types 3, 4 is suitably adapted to the other properties of the fibre types, such as for example the wettability of the fibres.

According to a preferred embodiment, the fibre length of the first fibre type 3 is between 0.3 mm and 1.5 mm and the fibre length of the second fibre type 4 between 1.5 mm and 5 mm. The first fibre type 3 may be constituted by polyolefin fibres, such as for example polyethylene or polypropylene. The second fibre type 4 may be constituted by all types of fibres exhibiting a higher liquid-conducting ability than the fibres of the first fibre type 3. Accordingly, the second fibre type 4 may be constituted by for example cellulose, viscose or polyester fibres. The second fibre type 4 may further be constituted by fibres treated with a wetting agent, such as for example fibres treated with surface active compounds, or fibres which in another way are treated in order to increase the wettability. The liquid-conducting/liquid-absorbing ability may also be increased by means of the second fibre type 4 being constituted by fibres exhibiting finer capillaries, i.e. fibres having a smaller pore radius than the fibres of the first fibre type. Further examples of fibres which are suitable for the second fibre type 4 are branched fibres, such as for example the fibres disclosed in WO 93/01779. Since fine external capillaries are created between the branched fibres, an increased liquid absorption ability is obtained. Another example of fibres which are suitable for the second fibre type 4 are fibres which create a better distance between the user and the liquid-absorbing fibres, such as for example fibres which collapse, i.e. shrink, when they are wetted. Other geometrical shapes resulting in a better distance and/or an increased liquid-absorption and liquid-conducting ability, respectively, are of course also applicable as fibres of the second fibre type 4.

The carrier layer 2 may be a single material layer or consist of a multilayered laminate. The carrier layer 2 shown in FIG. 1 is constituted by a multilayered laminate exhibiting a bottom layer 6 and a fibre fixation layer 5 to which the fibres 3, 4 are attached in one of their ends. The bottom layer 6 has a higher melting point than the fibre fixation layer 5 and consists of for example HDPE, polypropylene or another material suitable for the purpose. The fibre fixation layer 5 comprises for example LDPE, LLDPE, or other materials suitable for the purpose, exhibiting a lower melting point than the material in the bottom layer 6. The fibre fixation layer 5 may also consist of a gel which has the ability to absorb water, such as for example a gel of polyvinyl alcohol or a gel of polyacrylic acid.

The carrier layer 2 may also be constituted by a textile fibre fabric such as a hydrophillic nonwoven. Furthermore, the carrier layer 2 may be constituted by a surface, for example a surface on an absorbent body of foam, or on any other type of absorbent body having a sufficient integrity.

The fibres 3, 4 attach to the carrier layer 2 for example by means of being applied onto a melted fibre fixation layer, or by means of an adhesive such as for example hot-melt, a hydrophillic adhesive or any other adhesive suitable for the purpose. Furthermore, extruded fibres in a melted condition may be applied onto the carrier layer 2 and thereby eliminate the need for an adhesive. The attachment method has no major significance for the invention, but any previously known method to fixate fibres at an angle to a carrier surface may be used. The sanitary napkin 200 shown in FIG. 2 comprises a liquid-pervious cover layer 201 according to the invention, a liquid-impervious cover layer 205, and an absorbent body 206 enclosed between the cover layers. The liquid-impervious cover layer 205 comprises a plastic film, a fibre fabric rendered hydrophobic, a laminate of these materials, or any similar material suitable for the use, placed on the side of the sanitary napkin which is intended to be facing away from the user during use.

The absorbent body 206 enclosed between the cover layers 201, 205 is usually built up from one or several layers of cellulose fluff pulp. The cellulose fluff pulp may be mixed with fibres or particles of a highly absorbent polymeric material of the sort which during absorption chemically binds large quantities of liquid while forming a liquid-containing gel. Further components may be included in the absorbent body in order to improve the properties of the absorbent body 206. Examples of such components are binder fibres, shape-stabilizing components, or the like. The cover layers 201, 205 have a larger extension in the plane of the sanitary napkin 200 than the absorbent body 206, around the entire periphery of the absorbent body. The projecting portions 210 of the cover layers 201, 205 are mutually connected around the absorbent body 206, for example by means of gluing, welding, or in another way.

The liquid-pervious cover layer 201 has a similar construction as the liquid acquisition layer 1 shown in FIG. 1 and, accordingly, exhibits a carrier layer 202 onto which fibres 203, 204 are attached. The fibres 203, 204 are attached against the carrier layer 202 with one of their ends, and with the other, free end directed away from the carrier layer, by means of which the separate fibres are arranged at an angle α from the carrier Layer. The attachment angle is approximately 90° but may of course vary somewhat between the different fibres. The cover layer 201 is liquid-pervious because the carrier layer 202 exhibits perforations through the material, or because the carrier layer is constituted by a liquid-pervious material, such as for example a textile material. Furthermore, in cases where the absorbent body 201 exhibits sufficient integrity it may constitute a carrier layer 202, whereby the individual fibres attach directly to the side of the absorbent structure which is in closer contact with the user during use. The surface of the liquid-pervious cover layer exhibits a regularly alternating pattern. The regularly alternating pattern comprises separated regions of the longer fibres 203 and a continuous region of the shorter fibres 204.

Figure 2:
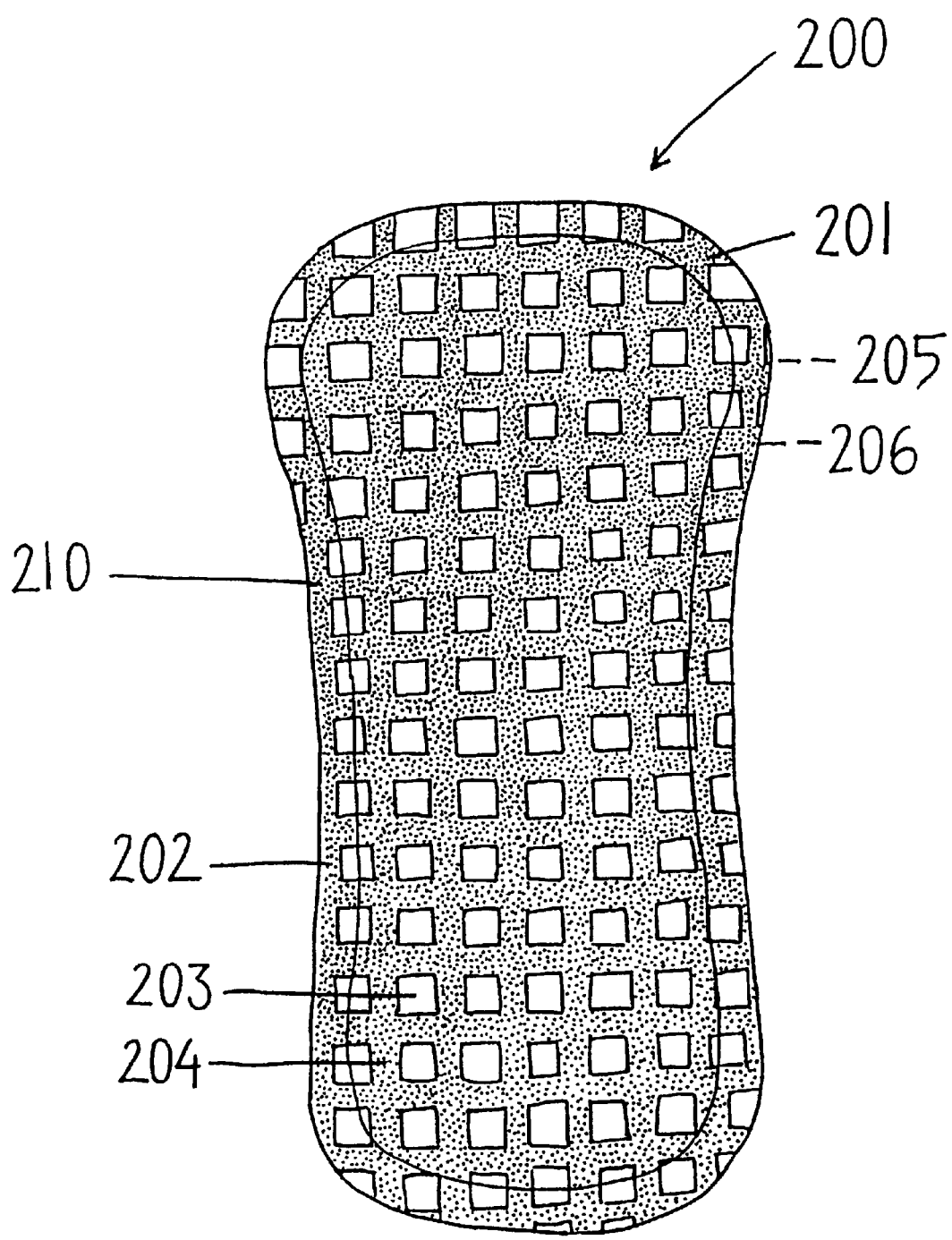
FIG. 2 shows a sanitary napkin with a cover layer according to the invention, seen from the side which is intended to be facing towards the user during use.
Figure 3:
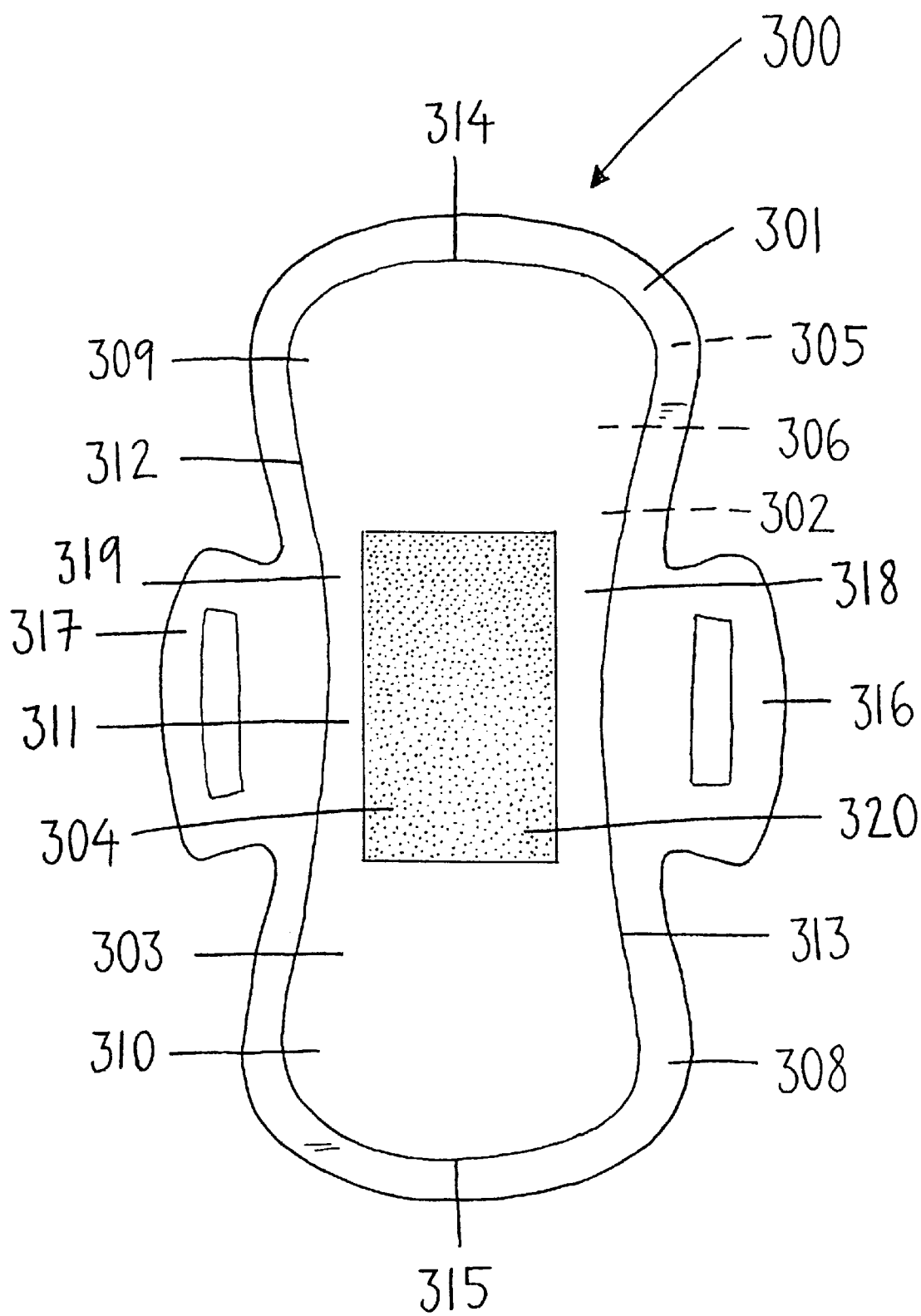
FIG. 3 shows another sanitary napkin according to the invention, seen from the side which is intended to be facing towards the user during use.

The sanitary napkin 300 shown in FIG. 3 has essentially the same construction as the sanitary napkin in FIG. 2. Accordingly, the sanitary napkin 300 exhibits an absorbent body 306 enclosed between a first, liquid-pervious cover layer 301, and a second, liquid-impervious cover layer 305.

The sanitary napkin 300 is hourglass-shaped, with wider end portions 309, 310 and a narrower crotch region 311 located in between. The crotch region 311 further exhibits two edge portions 318, 319 and a central portion 320 located therebetween. The central portion 320 of the crotch region 311 is the portion of the sanitary napkin which is intended to serve as a receiving surface for the body fluid which is excreted to the sanitary napkin during use. Furthermore, the absorbent body 306 has two longitudinal concavely-curved side edges 312, 313 and two transverse convexly-curved end edges 314, 315. The two cover layers 301, 305 have a slightly larger extension than the absorbent body 306 in the plane of the sanitary napkin 300 and the projecting portions 308 of the cover layers 301, 305 are mutually connected and form a continuous edge around the absorbent body 306. At the crotch portion 311 of the absorbent body 306 a side flap 316, 317 projects out from each of the longitudinal side edges 312, 313. The side flaps are formed by portions of the cover layers 301, 305 and, accordingly, each of the side flaps 316, 317 consists of a layer of liquid-pervious material and a layer of liquid-impervious material. The side flaps 316, 317 are intended to be able to be folded around the leg edges of the panties of the user during use.

The liquid-pervious cover layer 301 is built up in a similar way as the cover layers 1, 201 described, in FIGS. 1 and 2. Accordingly, the liquid-pervious cover layer 301 exhibits a carrier layer 302, onto which fibres 303, 304 are attached. The fibres 303, 304 are attached with one of their ends against the carrier layer, and with the other, free end directed away from the carrier layer, whereby the individual fibres are arranged at an angle α to the carrier layer. At the two end portions 309, 310 and within the edge portions 318, 319 of the crotch region, the liquid-pervious cover layer 301 primarily exhibits fibres of the first fibre type 303. The central portion 320 of this crotch region, on the contrary, primarily exhibits fibres of the second fibre type 304. By means of perforations through the carrier layer 302, or by means of the carrier layer 302 being constituted by an in itself liquid-pervious cover material such as for example a nonwoven, a cover layer 301 exhibiting liquid-permeability is created.

Figure 4:
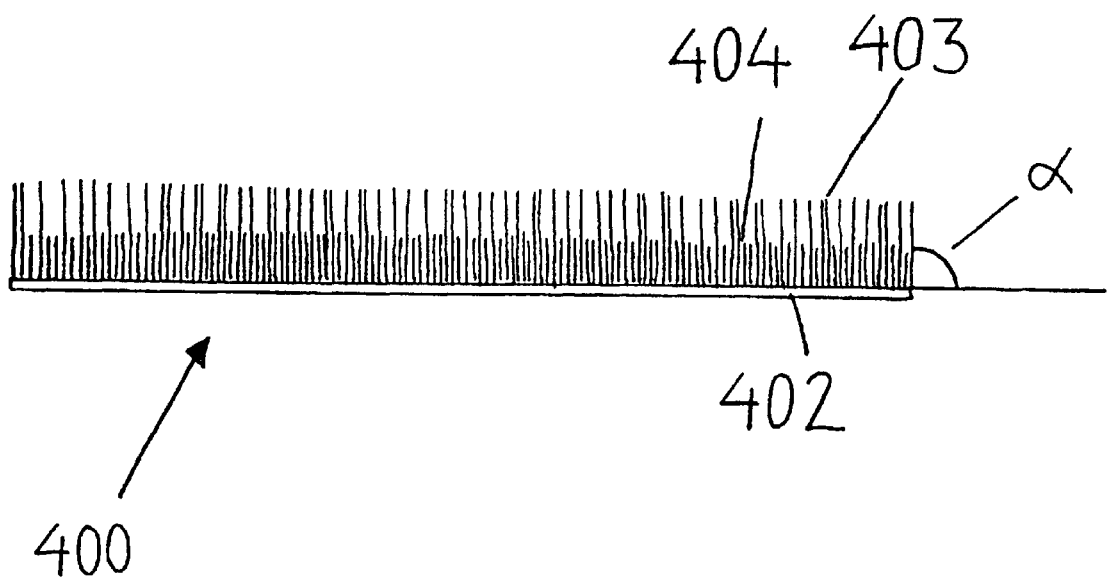
FIG. 4 shows another cross-section through a liquid acquisition layer according to the invention.

The liquid acquisition layer 400 shown in FIG. 4 has a similar construction as the liquid acquisition layer 1 shown in FIG. 1. Accordingly, the liquid acquisition layer 400 exhibits a carrier layer 402 onto which fibres 403, 404 are attached. The fibres 403, 404 are attached with one of their ends, while the other end is directed away from the carrier layer, by means of which the individual fibres are arranged at an angle α to the carrier layer. The attachment angle α is approximately 90°, but of course varies somewhat between the individual fibres. The fibres are attached to the carrier material for example by means of flocking whereby one of the fibre ends is attached against the carrier layer 402. The fibres 403, 404 further consist of a first fibre type 403 and a second fibre type 404 where the fibres of the first fibre type 403 are longer than the fibres of the second fibre type 404. The fibre types 403, 404 are uniformly distributed across the entire surface of the carrier layer 402. The carrier layer 402 consists of a plastic film or a multilayered laminate. Furthermore, the carrier layer 402 may consist of a nonwoven or any other textile fibre fabric, a foam material or another material suitable for the invention. The entire surface of the carrier material exhibits a uniform distribution of both fibres of the first fibre type 403 and fibres of the second fibre type 404.

Figure 5:
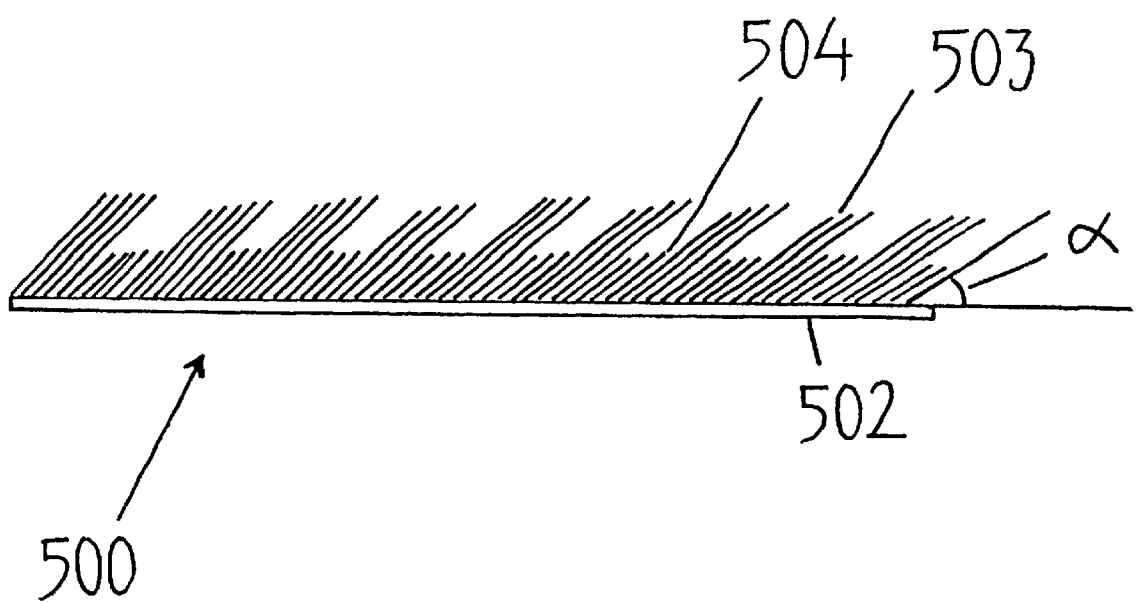
FIG. 5 shows another cross-section through a liquid acquisition layer according to the invention.

The liquid acquisition layer 501 shown in FIG. 5 has a similar construction as the liquid acquisition layers 1, 400 shown in FIGS. 1 and 4. Accordingly, the liquid acquisition layer 500 exhibits a carrier layer 502 such as the carrier layer 402 shown in FIG. 4 onto which fibres 503, 504 are attached. The fibres 503, 504 are attached with one of their ends, while the other, free end is directed away from the carrier layer 502, whereby the individual fibres 503, 504 are arranged at an angle α away from the carrier layer 502. The angle α between the individual fibres 503, 504 and the carrier layer 502 is between 30–70°, preferably approximately 45°. By means of the angle α between the carrier layer 502 and the individual fibres being smaller than 90°, the longer fibres 503 hide the shorter fibres 504 when the liquid acquisition layer 500 is viewed from above.

In the above-mentioned embodiments, the invention has been described with reference to sanitary napkins, but as mentioned before, the invention is of course also applicable for incontinence protectors, diapers, panty-liners, bed covers, seat covers and the like.

The invention further concerns all conceivable combinations of the above-mentioned embodiments, and is also applicable to other embodiments within the scope of the following claims.

What is claimed is:

1. A liquid acquisition layer for an absorbent article, comprising a carrier layer, said carrier layer having a first surface and a second surface, and
    individual fibers each exhibiting two fiber ends and being attached with one fiber end against said first surface of said carrier layer with an attachment angle α between the carrier layer and each individual fiber, said individual fibers being detached from each other,
    wherein the individual fibers comprise at least a first fiber type and a second fiber type, said first and second fiber types being different from each other.

2. The liquid acquisition layer according to claim 1, wherein the carrier layer is at least one of liquid-impervious and liquid-pervious.

3. Liquid acquisition layer according to claim 1, characterized in that the fibres of the first fibre type (3) are longer than the fibres of the second fibre type (4).

4. Liquid acquisition layer according to claim 1, characterized in that the fibres of the first fibre type (3) are between 1.5 mm and 5 mm long and that the fibres of the second fibre type (4) are between 0.3 mm and 1.5 mm long.

5. Liquid acquisition layer according to claim 1, characterized in that the attachment angle α between the carrier layer (2) and each individual fibre (3, 4) is between 30° and 90°.

6. Liquid acquisition layer according to claim 1, characterized in that the fibres of the second fibre type (4) are more hydrophillic than the fibres of the first fibre type (3).

7. Liquid acquisition layer according to claim 1, wherein the fibers of the second fiber type have a branched cross-section, so that the fibers of the second fiber type exhibit external capillaries.

8. Liquid acquisition layer according to claim 1, characterized in that the fibres of the second fibre type (4) collapse when wetted, as a result of which the height of the fibres of the second fibre type (4) is reduced when wetted.

9. Liquid acquisition layer according to claim 1, characterized in that the fibres of the second fibre type (4) are stiffer than the fibres of the first fibre type (3).

10. Liquid acquisition layer according to claim 1, characterized in that the liquid acquisition layer (2) exhibits an alternating pattern exhibiting separated regions of fibres of the first fibre type (3) and a substantially continuous region of fibres of the second fibre type (4).

11. Liquid acquisition layer according to claim 1, characterized in that the liquid acquisition layer (2) exhibits separated regions of fibres of the first fibre type (3) and separated regions of fibres of the second fibre type (4).

12. Liquid acquisition layer according to claim 1, characterized in that the liquid acquisition layer (2) exhibits continuous regions of fibres of the two fibre types (3, 4).

13. Liquid acquisition layer according to claim 1, characterized in that the liquid acquisition layer (1) exhibits a uniform distribution of both fibres of the first fibre type (3) and fibres of the second fibre type (4) across the entire surface of the carrier layer (2).

14. An absorbent article, comprising an absorbent body enclosed in a cover, at least a portion of the cover consists of a liquid-pervious cover layer, said cover layer comprising a carrier layer, said carrier layer having a first surface and a second surface, said cover layer further comprising individual fibers each exhibiting two fiber ends and being attached with one fiber end against said first surface of said carrier layer with an attachment angle α between the carrier layer and each individual fiber, said individual fibers being detached from each other,
    wherein the individual fibers comprise at least a first fiber type and a second fiber type, said first and second fiber types being different from each other.

15. Absorbent article according to claim 14, characterized in that the fibres of the first fibre type (203) are longer that the fibres of the second fibre type (204).

16. Absorbent article according to claim 14, characterized in that the fibres of the first fibre type (203) are more hydrophobic than the fibres of the second fibre type (204).

17. Absorbent article according to claim 14 and further exhibiting two end portions (309, 310) and a crotch region (311) located therebetween, characterized in that the liquid-pervious cover layer (301) at the crotch region (311) primarily exhibits fibres of the second fibre type (304) and that the liquid-pervious cover layer (301) at the end portions (309, 310) primarily exhibits fibres of the first fibre type (303).

18. Absorbent article according to claim 17 and further exhibiting two edge portions (318, 319) within the crotch region (311) and a central portion (320) located therebetween, characterized in that the liquid-pervious cover layer (301) within the central portion (320) of the crotch region (311) primarily exhibits fibres of the second fibre type (304) and that the edge portions (318, 319) of the crotch region (311) primarily exhibit fibres of the first fibre type (303).

19. An absorbent article comprising:
   a crotch region between first and second end portions;
   an absorbent body in the crotch region;
   a cover enclosing said absorbent body, said cover including a liquid-pervious layer and a carrier layer overlying said liquid-pervious layer; and
   a plurality of first and second fibers each having a first end attached to said carrier layer at a surface opposite said liquid-impervious layer at an attachment angle α, said plural first and second fibers being detached from each other, wherein
      said plural second fibers are only in the crotch region and said plural first fibers are only in the first and second end portions, and
      said plural first and second fibers are different from each other.

* * * * *